United States Patent [19]

Lee

[11] 4,387,227

[45] Jun. 7, 1983

[54] ZINC N,N'-ALKENYLSUCCINOYL DIPYRIDYL SUCCINATE AS ANTIOXIDANT

[75] Inventor: Richard J. Lee, Downers Grove, Ill.

[73] Assignee: Standard Oil Company (Indiana), Chicago, Ill.

[21] Appl. No.: 311,933

[22] Filed: Oct. 16, 1981

[51] Int. Cl.³ .................... C07D 401/04; C09K 15/32
[52] U.S. Cl. .................................. 546/5; 252/400 R
[58] Field of Search ................................... 546/5, 257

[56] References Cited

U.S. PATENT DOCUMENTS 3,147,262  9/1964  Kramer ........................... 546/257

Primary Examiner—Mark L. Berch
Attorney, Agent, or Firm—Richard A. Kretchmer; William T. McClain; William H. Magidson

[57] ABSTRACT

Novel zinc N,N'-alkenylsuccinoyl dipyridyl succinate is prepared by the novel reaction between an alkenylsuccinic anhydride, pyridine and zinc catalyzed by zinc chloride in pyridine reaction solvent. The novel zinc salt is useful to inhibit oxidation of hydrocarbon distillates and lubricant oils.

3 Claims, No Drawings

ZINC N,N'-ALKENYLSUCCINOYL DIPYRIDYL SUCCINATE AS ANTIOXIDANT

This invention relates to the subject zinc compounds as a novel composition of matter and novel oxidation inhibitor for lubricant oils. More specifically the invention relates the title compound whose alkenyl groups are preferably octadecencyl or dodecenyl and result from the novel reaction between an akenyl succinic anhydride or mixture of two different alkenyl succinic anhydrides with pyridine and zinc dust in the presence of zinc chloride hydrate as catalyst.

BACKGROUND OF THE INVENTION

According to Humphris and Scott (JCS Perkins II, pp 923-835, 1973) the mechanism for prevention of oxidation of hydrocarbons in air by oxidation inhibitors involves three stages. The first stage involves competition for dissolved oxygen molecules wherein a dissolved addition agent has the ability to utilize dissolved oxygen more effectively than the hydrocarbon in its formation of hydroperoxides as a first product. The second stage involves decomposition of said hydroperoxides faster than the thermal decomposition. Since hydroperoxide thermal decomposition can provide reactive radicals which are oxidation propagators, the dissolved addition agent should provide a chain-transfer capacity which terminates reactive radicals into non-propagating species.

Those three effects have been, in general, accomplished by the use of two or more hydrocarbon-soluble addition agents each performing to its own capacity and advantage in a concerted, compatible effort to make up for the weakness of the other addition agents present. For example, a hindered phenol is used in combination with a phosphosulfurized hydrocarbon (an acidic product of the reaction of $P_2S_5$ with a medium to long chain mono-olefin) or salt thereof. At times the combination of addition agents in hydrocarbons (distillate fuels and lubricant oils) have been quite subtle in their combined effects. While one or two might be recognized as oxidation inhibitors, each may totally lack one of the three above activities, for example chain-transfer. However, another type of addition agent, for example, an anti-rust, anti-corrosion or anti-wear or detergent agent may also have some chain-transfer capacity and terminate reactive radicals into non-propagating species. Such subtly active compounds used in the past were metal-containing compounds. Now the trend is to decrease at least to a minimum, if not entirely, the use of ash deposit forming metal-containing addition agents for distillate fuels (gasoline, diesel fuel, heating oils) and lubricant oils. The search for so-called ash-free hydrocarbon addition agents since the early 1960's has brought to light the exacting requirements for necessary effects by addition agents. For example, the early use of "ash-free" detergent addition agents such as amine derivatives (amides, imides and amidines) of an organic carboxylic acid (e.g., oil-soluble, long chain-containing succinnic acid or anhydride), or a Mannich base derived from the condensation of a hydrocarbon-soluble alkylkphenol, an aldehyde and an amine brought with it the unexpected "thermal thickening" which was really a result of hydrocarbon oxidation. Such thickening was most pronounced in crankcase lubricant oils where the lubricant oil formulation would suddenly increase in viscosity and take on a gel-like or mayonnaise-like appearance.

So far the trend for using an "ash-free" oxidation inhibitor has included the use of a known "ash-free" ion-radical catalyst for hydroperoxide decomposition. Hindered phenols or phosphites thereof, which are of the ash-free type, are used for their in situ ion-radical formation for catalytically decomposition of hydroperoxide.

We have now discovered a single additive species which possesses the three before-mentioned activities of fast utilization of oxygen dissolved in hydrocarbon, exert some catalytic activity for hydroperoxide decomposition and chain-transfer to terminate reactive radicals to non-propagating species. We have not in our search of the pertinent art found any reference to said additive species either per se or its use in hydrocarbons to suppress their oxidation. Hence we believe the inventive additive species to be a novel composition of matter, its preparation to be novel, and its use as a hydrocarbon oxidation inhibiting agent as well to be novel.

SUMMARY OF THE INVENTION

The present inventive novel composition of matter comprises a zinc N,N'-alkenylsuccinoyl dipyridyl succinate which has the formula:

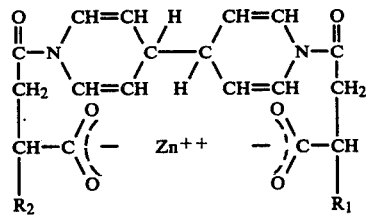

wherein $R_1$ and $R_2$ are alkenyl hydrocarbon groups. $R_1$ and $R_2$ can be the same or different alkenyl hydrocarbon groups. Preferably the alkenyl hydrocarbon groups contain inclusively twelve to eighteen carbon atoms as in the dodecenyl and octadecenyl hydrocarbon groups. The novelcomposition, while not "ash-free" has a very low zinc content so that, when used at normal anti-oxident levels of one to five weight percent, the hydrocarbon in which the composition is used has an insignificant zinc content, less than 0.5 weight percent.

Said novel zinc N,N'-alkenylsuccinoyl dipyridyl succinate composition of matter is formed by the novel reaction between pyridine, one or two alkenyl-substituted succinic anhydrides and zinc (in dust form) in the presence of zinc chloride hydrate as catalyst. The reaction is carried out twice. The first reaction is carried out with a large excess of pyridine both as reactant and reaction solvent first at the boiling point temperature of pyridine (115°–116° C.) and then at increasing temperature to 160° C. while distillatively removing about 70 to 80% of the initially used excess of pyridine. The second reaction involves the use of fresh pyridine in smaller excess (20 to 40% of that first used), additional zinc and additional zinc chloride hydrate catalyst at a reaction temperature of 160° C. maximum while again distillatively removing unreacted pyridine. The filtrate of the residual material will contain 80 or more weight percent of the novel composition of matter.

The novel coupling of two molecules of pyridine while decreasing the unsaturation of the molecules is facile and rapid and likely occurs in the first reaction step after zinc has opened the anhydride rings.

As an oxidation inhibitor the present inventive, novel compositions undergo the six reactions to follow shown in simplified manner excluding the zinc-alkenylsuccinate bridge. The radical-cation represented by formula (II) is believed to function, like other known ion-radicals, as a catalyst for hydroperoxide decomposition.

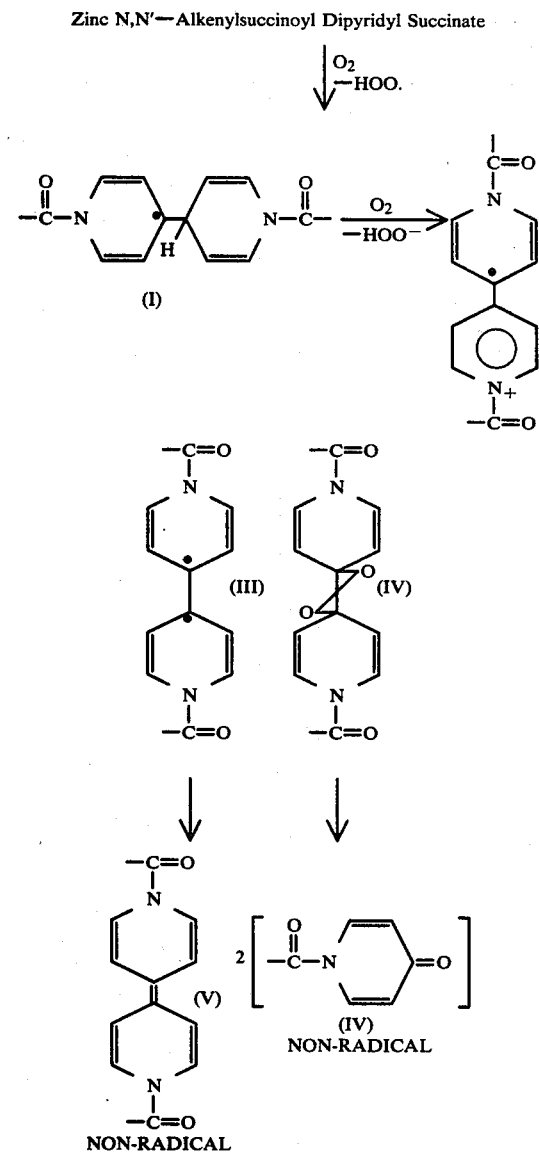

At a given instant species (I), (II), and (III) may all be present. Hence species (I) and (III) are oxygen scavengers, and species (II) is the catalyst for peroxide decomposition. Species (IV), (V), and (VI) are good chain-transfer radical terminaters. The foregoing theory, while believed to be technically plausible, has no effect on the operability or merit of the present inventive compositions.

The following example illustrates the present inventive compositions as well as one preferred specie and illustrates the preparative method therefore.

EXAMPLE 1

In this preparation of one preferred illustrative specie of the present inventive composition, two different alkenylsuccinic anhydrides are used so that by later analytical procedures it may be determined whether the concept related to the novel composition and to its preparation might be technically plausible.

In a five liter flask fitted with a stirring device and adapted to be attached to a distillation column there are added 557 grams (1.62 gram moles) of iso-octadecenyl succinic anhydride, 325 grams (1.21 gram moles) of dodecenyl succinic anhydride and one liter (19.09 gram moles) of pyridine. The resulting mixture is stirred and to the stirred fluid there are added 155 grams (2.37 gram atoms or 4.74 gram equivalents) of zinc in dust form. Such amount of zinc represents a 1.9 gram equivalent excess over that required to react with each anhydride ring and form a zinc bis (succinoyl succinate) structure. Also five grams of zinc chloride hydrate as catalyst is added to the stirred suspension of zinc dust. The flask is attached to a water cooled reflux condenser and the flask's stirred contents are heated to pyridine's boiling point (115°–116° C.) temperature. The condensed pyridine returned to the flask as reflux liquid. The reaction mixture is held under such reflux conditions for six hours. The flask is attached to the distillation column and then 800 ml of pyridine are distilled off to a residue temperature of 160° C.

The residue is cooled to 100° C. and there are added thereto 300 ml of pyridine, 65 grams (0.994 gram atom) of zinc and 5 gram of zinc chloride hydrate. This second mixture is stirred and heated slowly back to a temperature of 160° C. while the flask is attached to the distillation column. This time all the unreacted pyridine is distilled off.

When removal of the pyridine is complete, the hot pyridine-free portion of the reaction mixture is filtered to remove salts and unused zinc. A sample of the filtrate is subjected to chromatographic and infrared analyses. Such analysis indicated the presence of the type of compound shown as zinc N,N'-alkenylsuccinoyl dipyridyl succinate at about 80 weight percent. Analysis for zinc content shows the presence of 7.5 weight percent zinc while the theoretical zinc content for the composition having one octadecenyl ($R_1$) group and one dodecenyl ($R_2$) group is 7.8 weight percent.

The compositions of the present invention are effective oxidation inhibitors in distillate fuels and oleaginous lubricant compositions when used in amounts of from 0.1 to 10 weight percent. Suitable lubricating base oils are mineral hydrocarbon oils, i.e., petroleum oils; synthetic oils such as the sebacate esters, adipate esters and synthetic hydrocarbon oils produced by polymerization of olefinic hydrocarbons. Concentrates of suitable oil bases containing from 10 to 75% by weight or more of the present inventive compositions can be used for blending with base lubricating oils in proportions desired for particular use conditions. Such lubricant oil formulations can also contain other well known addition agents to impart other desired properties to the formulations.

UTILITY EXAMPLE

Two oil formulations of the SAE 10W-30 type are prepared. Each formulation contains the same base oils, viscosity index improvement addition agent, the same "ashless type" dispersant-detergent addition agent, the same anti-wear addition agent, and the same rust inhibitor agent. The only difference between the formulations is that Formulation A contains 2.0 wt. % of a commercially used oxidation inhibitor and its commonly used phosphosulfurized adjunct and Formulation B contains an equivalent amount, 1.9 weight percent of the product of Example 1 with its adjunct. Each formulation is heated to a temperature of 171° C., maintained at that temperature while air at the rate of 60 ml per minute (volume at 20° C. and 1.0 atmosphere) is injected into the hot oil until the viscosity of the oil (measured at 20° C.) has quadrupled (4Vo). Formulation A reached 4Vo in 46 hours while Formulation B reached 4Vo in 113 hours.

The invention claimed is:

1. A zinc N,N'-alkenylsuccinoyl dipyridyl succinate having the formula:

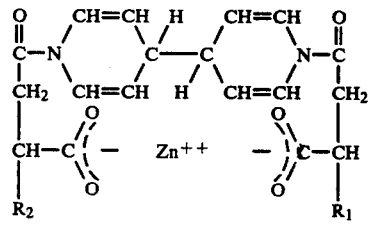

wherein each of $R_1$ and $R_2$ are alkenyl hydrocarbon groups.

2. The compound of claim 1 wherein each of $R_1$ and $R_2$ are alkenyl hydrocarbon groups containing from 12 to 18 carbon atoms.

3. The compound of claim 1 wherein $R_1$ is the dodecenyl group and $R_2$ is the octadecenyl group.

* * * * *